United States Patent [19]

Ogawa et al.

[11] Patent Number: 4,884,448
[45] Date of Patent: Dec. 5, 1989

[54] ULTRASONIC DOPPLER METER

[75] Inventors: Toshio Ogawa; Hisashi Nishiyama; Kageyoshi Katakura, all of Tokyo; Shizuo Ishikawa, Kanagawa, all of Japan

[73] Assignee: Hitachi Medical Corporation, Tokyo, Japan

[21] Appl. No.: 230,972

[22] Filed: Aug. 11, 1988

[30] Foreign Application Priority Data

Sep. 24, 1987 [JP] Japan .................. 62-237211

[51] Int. Cl.$^4$ .......................................... G01N 29/00
[52] U.S. Cl. .................. 73/597; 128/661.09
[58] Field of Search ............... 73/597, 602, 627, 629; 128/660.01, 661.08, 661.09

[56] References Cited

U.S. PATENT DOCUMENTS 4,771,789 9/1988 Namekawa ..................... 128/661.09

FOREIGN PATENT DOCUMENTS 62-169073 7/1987 Japan .

OTHER PUBLICATIONS

"Application of the Phase Detection Principle in a Transcutaneous Velocity Profile Meter", by M. Brandestini, Proc. of the 2nd Europ. Congress on Ultrasonics, p. 144, 1975.
JP-A-62-169072 (Corresponding to U.S. Patent Application Ser. No. 5,900 filed Jan. 22, 1987).
"Blood Flow Imaging Using a Discrete-Time Frequency Meter", by M. Brandestini et al., 1978 Ultrason. Symp. Proc. IEEE, Cat. #78, Ch. 1344-1SU.
"Color-Coded Blood Flow Imaging System Using Ultrasound Doppler" by K. Namekawa et al., 1985 (Corres. to English version, Real-Time Two-Dimensional Blood Flow Imaging Using an Autocorrelation Technique.
IEEE Trans. on Sonics and Ultrasonics vol. SU-32, No. 3, May 1985, U.S. Patent Application No. 101,444 filed Sep. 29, 1987 (corres. to JP-A-63-84533).

Primary Examiner—Stewart J. Levy
Assistant Examiner—Louis M. Arana
Attorney, Agent, or Firm—Antonelli, Terry & Wands

[57] ABSTRACT

A ultrasonic Doppler meter for measuring the speed of a moving body by measuring the phase shift due to the Doppler effect on received signals, comprising a transmitting/receiving unit transmitting ultrasonic bursts with a constant time interval towards the moving body and receiving reflected waves; a unit for measuring a phase difference vector representing a difference between phases of received signals corresponding to two successive transmitted pulses; a unit for calculating a difference between phase differences on the basis of two successive phase difference vectors stated above; and an accumulation unit for adding the difference between phase differences to a preceeding phase difference vector so as to obtain the speed of the moving object.

3 Claims, 6 Drawing Sheets

ULTRASONIC DOPPLER METER

BACKGROUND OF THE INVENTION

This invention relates to an apparatus for detecting the velocity of an object by using ultrasonic waves and in particular to an apparatus for measuring the blood flow speed in a living body in real time.

There are known various types of devices for measuring the flow speed of an object by use of the Doppler effect of acoustic waves. In particular, in an apparatus using the pulse Doppler method, by which the phase difference is detected, it is possible to measure the velocity of each of a plurality of parts over the whole measurement range in real time by sending transmitted pulses in the form of a burst and by measuring the phase difference of received signals for every interval of the transmitted pulses. An apparatus similar thereto is described e.g. in "Application of the phase detection principle in a transcutaneous velocity profile meter" by M. Brandestini, Proc. of the Second European Congress on Ultrasonics in Medicine, p. 144, 1975.

According to the pulse Doppler method described above, denoting the repetition period of the transmitted wave as T, the highest measurable Doppler frequency shift $F_d$ is equal to $\frac{1}{2}T$. On the other hand, denoting the propagation velocity of an acoustic wave (sound velocity) as C, the measurable depth D is represented by $TC/2$. Consequently, the product of $F_d$ and D is constant and equal to $C/4$ and the measurable velocity or the measurable depth is therefore limited. For the purpose of increasing the highest measurable Doppler frequency shift $F_d$, U.S. patent application No. 5,900 was filed Jan. 22, 1987, claiming priority based on Japanese patent application No. 61-10117 filed Jan. 22, 1986 and laid-open on July 25, 1987 (JP-A-62-169073). The corresponding DE patent application No. P3701786.1 was filed Jan. 22, 1987 and laid open on Aug. 6, 1987. In these patent applications it is proposed that transmitted pulse intervals are made unequal such as $T-T_s$ and $T+T_s$ and that the Doppler shift ($\omega_d$) is obtained according to the following formula:

$\omega_d$=(difference between phase differences)/$2T_s$, where $T_s \neq 0$.

According to this method, it is possible to increase the highest measurable Doppler frequency shift by reducing $T_s$. However, this method has problems such as degradation in the signal to noise ratio (S/N ratio), complication of the structure of moving target indicator filters (hereinbelow called MTI filters), etc. Concerning the former problem, denoting the unequal time interval ratio $2T_s/T$ as $\alpha$, the noise component increases inversely proportionally to $\alpha$. Concerning the latter, in the case where there are two sorts of unequal intervals, i.e. $T-T_s$ and $T+T_s$, as described previously, so-called blind speeds, which are measured to be zero although the object is, in reality, moving, arise at $n/(2T+T_s)$ (n=1, 2, . . . ). In order to resolve this problem it is necessary to use more than 2 sorts of pulse intervals such as $T-T_s$, T and $T+T_s$, which complicates the structure of the MIT filters.

Reference may be made to "BLOOD FLOW IMAGING USING A DISCRETE-TIME FREQUENCY METER" by M. A. Brandestini et al., 1978 Ultrasonics Symposium Proceedings, IEEE Cat. #78 CH 1344-1SU.

SUMMARY OF THE INVENTION

An object of this invention is to provide a Doppler meter, by means of which it is possible to measure the velocity of an object with a high S/N ratio even for deep portions (i.e. portions fairly distant from the probe) which is moving at high speeds.

Another object of this invention is to provide a Doppler meter having a simple structure.

According to an aspect of this invention, the vector representing the phase difference (corresponding to the Doppler frequency or the speed of the object to be measured) between two respective adjoining received signals each produced for every interval between two adjacent transmitted pulses, is obtained and further the difference between consecutive two phase differences {i.e. corresponding to the difference between two adjacent Doppler frequencies (hereinbelow called differential Doppler frequency) or to the acceleration of the object} is calculated. Then instantaneous Doppler frequencies are obtained in such a manner that the first differential Doppler frequency is added to an initial Doppler frequency obtained immediately after the start of the speed measurement to thereby obtain the second Doppler frequency; the second differential Doppler frequency is added to the thus obtained second Doppler frequency to thereby obtain the third Doppler frequency; and so forth. In this way it is possible to measure accurately successively the speed of a body moving with a high speed by transforming these instantaneous Doppler frequencies into the speed.

DESCRIPTION OF THE PREFERRED EMBODIMENTS

Figure 1:
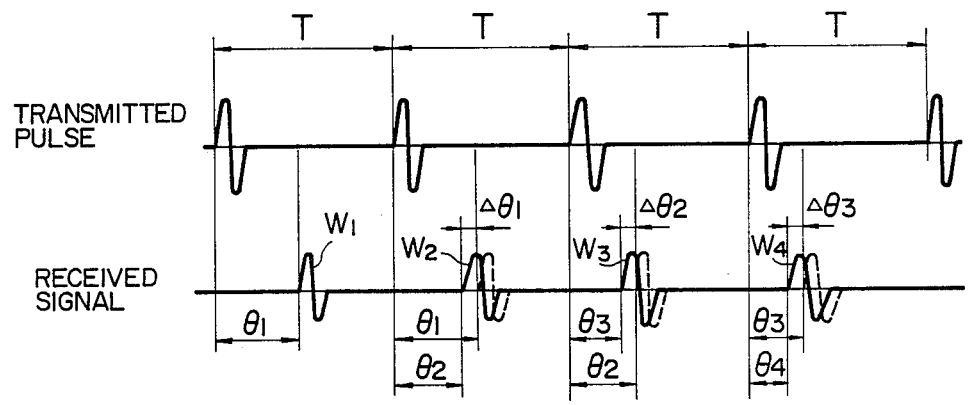
FIGS. 1 and 2 are diagrams useful for explaining the principle of this invention.
Figure 2:
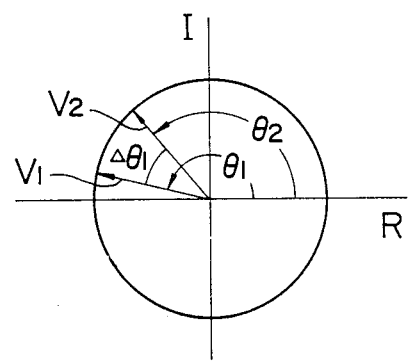

Hereinbelow the principle of this invention will be explained, referring to FIGS. 1 to 3. FIG. 1 shows the relation between transmitted pulses and received signals; FIG. 2 indicates polar coordinates representing vectors corresponding to the received signals; and FIG. 3 shows an example of the circuit construction preferable for obtaining vectors of received signals.

Transmitted pulses are successively produced with a predetermined constant time interval. A wave of a transmitted pulse, which is reflected by an object to be measured and received by a probe 6, is amplified by a high frequency amplifier 7 through a transmission/reception switching circuit 5 and outputted as a received signal (FIG. 3). The first received signal has a phase $\theta_1$; the second $\theta_2$; the third $\theta_3$; the fourth $\theta_4$; and so forth. $\Delta\theta_1, \Delta\theta_2, \Delta\theta_3, \ldots$ represent variations in the phase (phase differences) in a period of time of T.

In FIG. 2, vectors $V_1$ and $V_2$ of received signals $w_1$ and $w_2$ are indicated on polar coordinates. How vectors $V_1, V_2, \ldots$ are generated will be explained, referring to FIG. 3.

Figure 3:
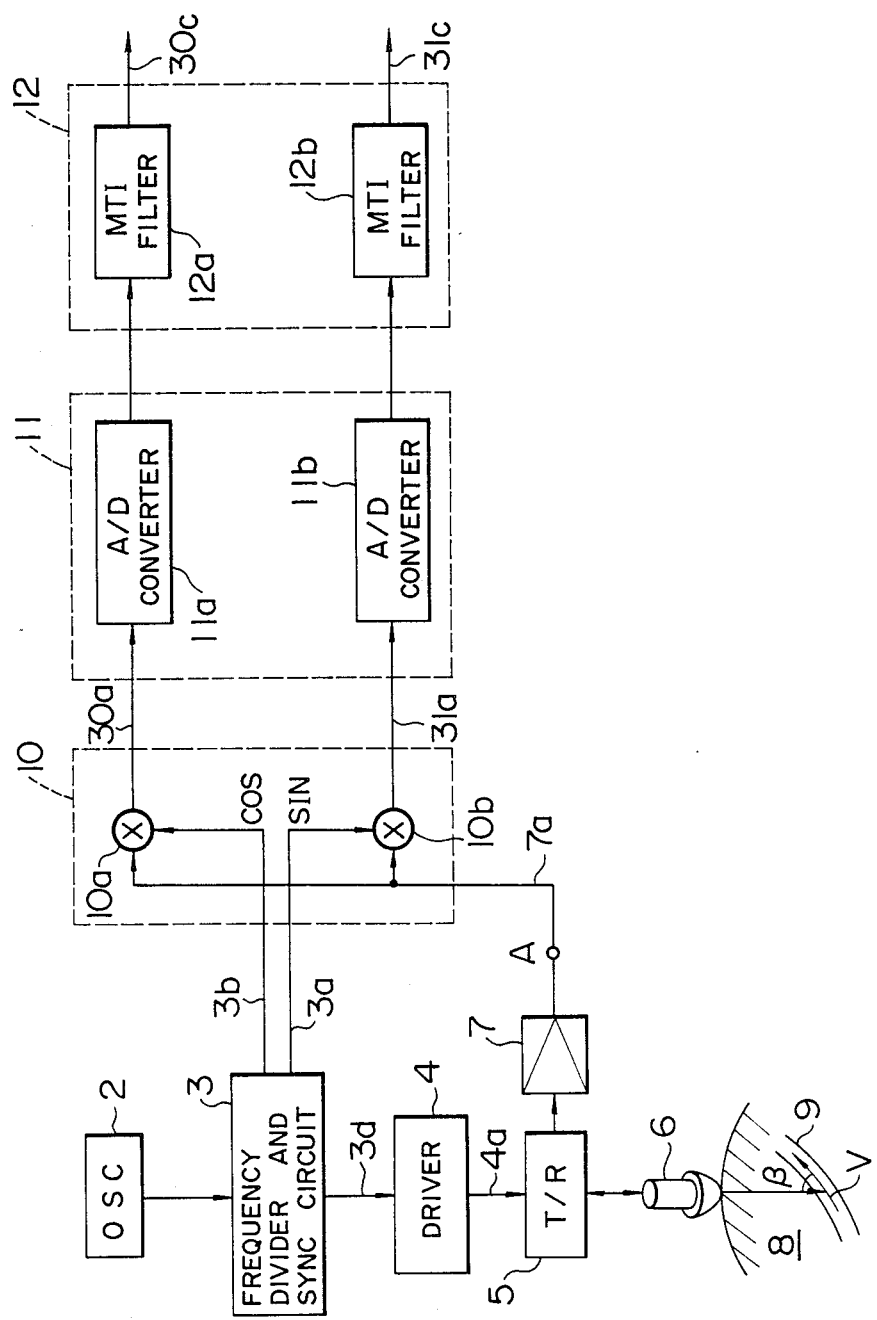
FIG. 3 is a block diagram illustrating a part of a ultrasonic Doppler meter according to this invention.

In FIG. 3, the output of an oscillator 2 generating a stable high frequency signal is given to a frequency divider and synchronizer circuit 3. The circuit 3 outputs a pulse signal 3d for transmission of a ultrasonic pulse beam, as well as a sine wave 3a and a cosine wave 3b for the transformation into the polar coordinates.

The period of the pulse signal 3d for transmission is reduced e.g. to a half by a driving circuit 4 and are supplied to the probe 6 through a transmission/reception switching circuit 4 so as to excite the probe 6 so that the ultrasonic pulse beam is sent to a blood vessel 9 in a body 8 to be examined.

The reflected signal from the body 8 to be examined is transformed into an electric signal by the probe 6, sent to a high frequency amplifier 7 through the transmission/reception switching circuit 5, where it is amplified, and is given to a demodulator or mixer 10 including a polar coordinate detector 10a and 10b as a received input signal 7a.

The received input signal 7a ($w_1, w_2, w_3, \ldots$ in FIG. 1) is given to multipliers 10a and 10b constituting the polar coordinate detector, where the cosine and the sine waves coming from the frequency divider and synchronizer circuit 3 are multiplied so as to obtain analoque R and I components 30a and 31a.

These analoque signals are digitized by an A/D converter 11 including A/D converters 11a and 11b and thus digitized R (real) and I (imaginary) components 30c and 31c are obtained through an MTI filter 12 including filters 12a and 12b.

Using these R and I components, the received signal Z is expressed, in general, by:

$$Z = R + jI$$
$$= A\exp(j\theta)$$
$$\text{where } A = \sqrt{R^2 + I^2}$$
$$\theta = \tan^{-1}\left(\frac{I}{R}\right).$$

In this application, the vector $V_i$ of the received signal at the time of the i-th repetition pulse is represented by:

$$V_i = \exp(j\theta_i)$$

where the factor of amplitude A is omitted for ease of explanation.

Figures 4A, 4B:
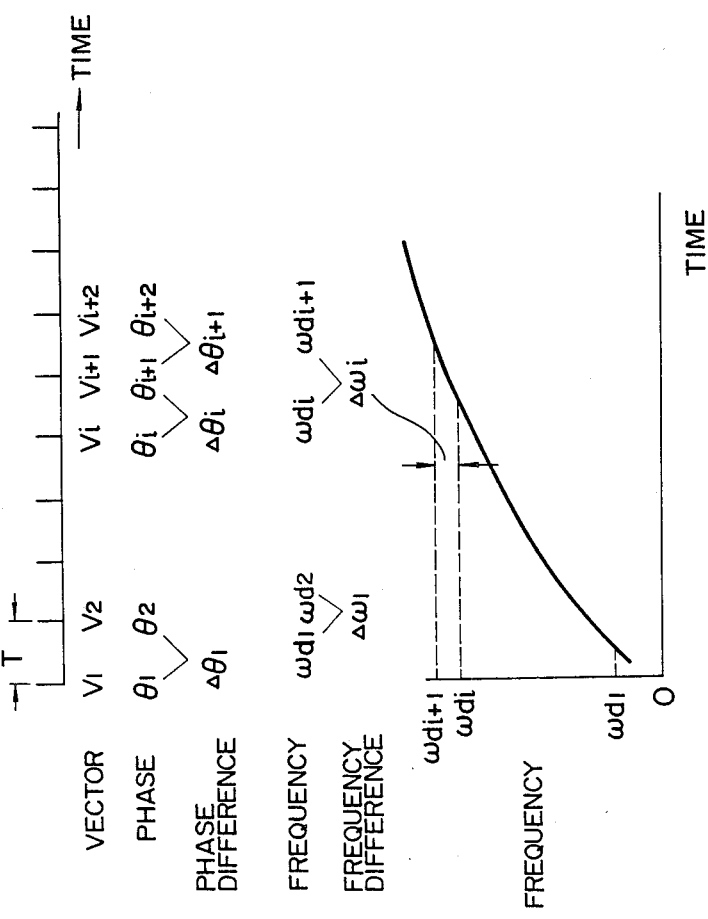
FIGS. 4A and 4B are diagrams useful for explaining the principle of this invention.

FIGS. 4A and 4B are for explaining this invention. In the figure, transmitted pulses are transmitted with a constant time interval corresponding to a repetition period T. As stated previously, the vector of the received signal from moving blood cells is represented by $V_i$ and the phase thereof by $\theta_i$. Then the variation in phase (phase difference) $\Delta\theta_i$ in a time T is obtained, which has the following relationships to the Doppler frequency $\omega_{di}$:

$$\omega_{di} = [2\omega_o/C] \cdot V \quad (1)$$
$$= \Delta\theta_i/T \quad (2)$$
$$= (\theta_{i+1} - \theta_i)/T, \quad (i = 0, 1, 2, \ldots) \quad (3)$$

where
T: pulse repetition period
V: speed of blood cells
$\omega_o$: frequency of supersonic wave
C: sound velocity.

The above-mentioned speed measurement is an already known prior art technique. According to this invention, the difference $\Delta\omega_i$ between Doppler frequencies $\omega_{di}$ (differential Doppler frequency) is further measured. As it can be understood from FIGS. 4A and 4B, between the Doppler frequency $\omega_{di}$ and the differential Doppler frequency $\Delta\omega_i$ there exists the following relationship:

$$\Delta\omega_i = \omega_{d,i+1} - \omega_{di} \quad (4)$$

where $i = 0, 1, 2, \ldots$. Consequently, when a Doppler frequency $\omega_{do}$ is given as the initial condition, it is possible to obtain the Doppler frequency $\omega_{di}$ at each of points of time one after another by adding the measured $\Delta\omega_o$ to $\omega_{d0}$ to obtain $\omega_{d1}$; adding the measured $\Delta\omega_1$ to the thus obtained preceeding $\omega_{d1}$ to obtain $\omega_{d2}; \ldots$; adding the measured $\omega_{i-1}$ to the preceeding $\omega_{d,i-1}$ to obtain $\omega_{di}$.

Now an embodiment of this invention will be explained.

Figure 5:
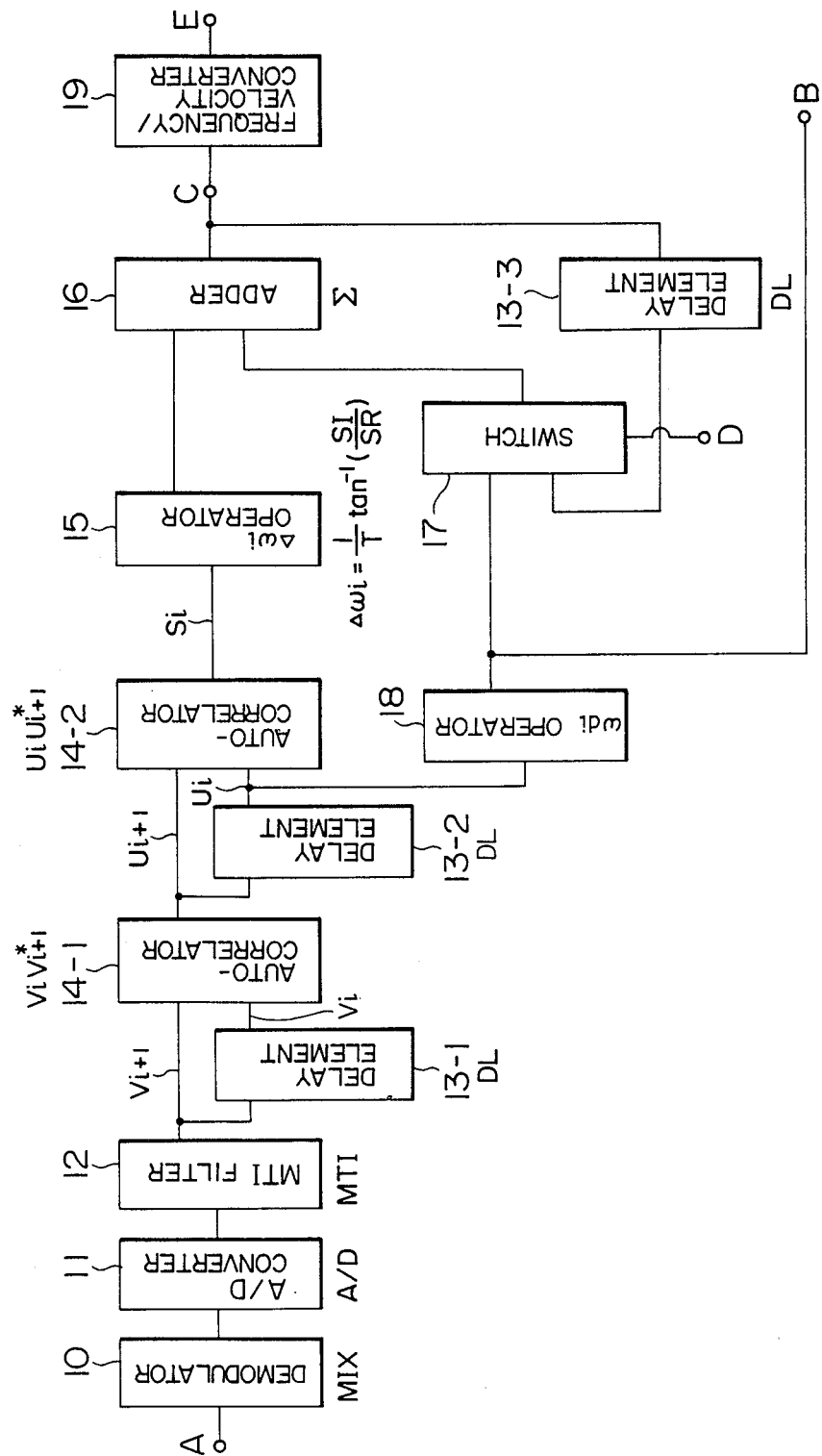
FIG. 5 is a block diagram useful for explaining an embodiment of this invention.

FIG. 5 is a block diagram illustrating an embodiment of this invention, in which reference numeral 10 is a demodulator (mixer), 11 is an A/D converter; and 12 is an MTI (moving Target Indicator) filter. These are identical to those indicated by 10, 11 and 12 in FIG. 3, respectively, and therefore they are referred to with the same reference numerals. One output line of the MTI filter 12 in FIG. 5 represents the R and the I components 30c and 31c of the MTI filter 12 in FIG. 3.

13-1, 13-2 and 13-3 are delaying elements; 14-1 and 14-2 are a first and a second auto-correlation operator; 15 is a differential Doppler frequency $\Delta\omega_i$ operator; 16 is an adder; 17 is a switch; and 18 is a Doppler frequency $\omega_{di}$ operator. Although usually the signal to noise ratio is improved by an averaging process of sequentially derived outputs of the first auto-correlation operator 14-1, this approach is not adopted in this embodiment. However the following explanation remains unchanged and valid, even if this averaging process were to be included in the first auto-correlation operator 14-1. A terminal A is a received wave signal input terminal, which is connected with the output terminal A of the amplifier 7 in FIG. 3. 19 is a converter converting the Doppler frequency into the speed. A terminal B is an output terminal, through which the Doppler frequency calculated by using Eq. (3) according to the prior art technique is outputted; a terminal C is an output terminal, through which the Doppler frequency according to this invention is outputted; and a terminal D is an input terminal, through which the signal controlling the switch 17 is inputted. The switch 17 is so switched over that the output of the Doppler frequency operator 18 is inputted to the adder 16 when there exists the control signal and the output of the delaying element 13-3 is inputted to the same adder 16 when there exists no control signal. Further, the output of the Doppler frequency operator 18 is one input of the switch 17 and the output of the adder 16 is inputted in the other input of the switch 17 through the delaying element 13-3. In this way a signal representing the speed corresponding to the measured Doppler frequency is obtained at an output terminal E.

Figure 8A:
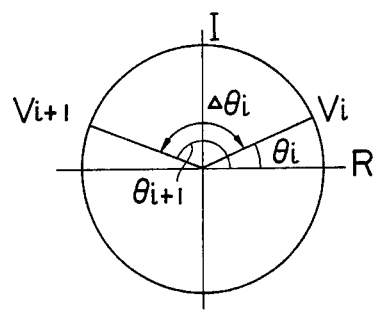

In such a structure, as described above, the received wave signal is inputted through the terminal A and demodulated separately to the real part and the imaginary part. The demodulated signals are digitized by the A/D converter 11 and inputted to the MTI filter. As already well known, received strong wave signals coming from fixed objects are removed by the MTI filter, which outputs only received weak wave signals coming from blood cells. As indicated in FIGS. 4A and 4B as well as in FIG. 8A, and further as described previously, the vector $V_i$ of the received wave signal at the time of the i-th repetiton pulse is expressed by:

$$V_i = \exp(j\theta_i) \qquad (5)$$

where $\theta_i$ represents the phase and the factor of amplitude is omitted for the sake of simplicity (refer to FIG. 8A).

A phase difference vector $U_i$ is obtained by the delaying element 13-1 and the first auto-correlator 14-1, as follows:

$$\begin{align}
U_i &= V_{i+1} \cdot V_i^* \text{(*: conjugate complex)} \qquad (6)\\
&= \exp(j\Delta\theta_i), (\Delta\theta_i = \theta_{i+1} - \theta_i) \qquad (7)\\
&= U_R + jU_I, (U_R\text{: real part, } U_I\text{: imaginary part}) \qquad (8)
\end{align}$$

Figure 8B:
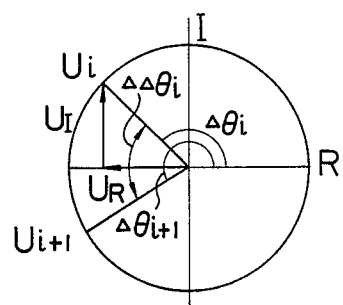
Figure 8C:
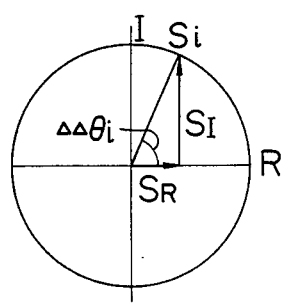

(refer to FIGS. 8A and 8B)

The auto-correlator is well known and it can be realized e.g. by the circuit indicated in FIG. 3 in "Color-Coded Blood Flow Imaging System Using Ultrasound Doppler" by K. Namekawa et al., 1985 (corresponding to English version "Real-Time Two-Dimensional Blood Flow Imaging Using an Auto correlation Technique" IEEE TRANS. ON SONICS AND ULTRASONICS, Vol. SU-32 No. 3, May 1985).

This phase difference vector $U_i$ is inputted to the Doppler frequency operator 18 and the Doppler frequency $\omega_{di}$ is obtained by:

$$\omega_{di} = \frac{1}{T} \tan^{-1} \frac{U_I}{U_R}, \qquad (9)$$

which is outputted through the terminal B. This is a measurement of the Doppler frequency by a prior art method. The measurement is effected in a domain from $\pi/T$ to $\pi/T$. The Doppler frequency outside of these domains is subjected to so-called aliasing, which gives rise to erroneous operations.

According to this invention the Doppler frequency operator 18 is used only for obtaining the Doppler frequency initial value $\omega_{do}$ stated later and based on the phase difference vector, the following processing is effected so as to obtain an exact Doppler frequency.

That is, the vector $S_i$ representing the difference between phase differences can be obtained by the delaying element 13-2 and the second auto-correlator 14-2, as given by the following equation:

$$\begin{align}
S_i &= U_{i+1} \cdot U_i^* \qquad (10)\\
&= \exp(j\Delta\Delta\theta_i), (\Delta\Delta\theta_i = \Delta\theta_{i+1} - \Delta\theta_i) \qquad (11)\\
&= S_R + jS_I
\end{align}$$

This vector $S_i$ representing the difference between phase differences is inputted to the differential Doppler frequency operator 15 and the differential Doppler frequency $\Delta\omega_i$ is obtained by using $$\Delta\omega_i = \frac{1}{T} \tan^{-1}\left(\frac{S_I}{S_R}\right), \qquad (13)$$

which is supplied to one input of the adder 16.

An accumulator consisting of the adder 16, the switch 17, the $\omega_{di}$ operator 18 and the delaying element 13-3 operates on the basis of this $\Delta\omega_i$, as follows, so as to calculate the Doppler frequency.

At first a control signal is inputted in the control terminal D of the switch 17 and $\omega_{do}$ is added to the adder 16 through the switch 17 by selecting the output (initial value) $\omega_{do}$ of the Doppler frequency operator 18, where the Doppler frequency $\omega_{d1}$ is obtained by adding the first output $\Delta_o$ from the differential Doppler frequency operator 15 to $\omega_{d0}$, as follows:

$$\omega_{d1} = \Delta\omega_o + \omega_{d0}.$$

Then the output of the adder 16 is inputted to the adder 16 through the delaying element 13-3 and the switch 17 by removing the control signal at the terminal D and selecting the output of the delaying element 13-3, and the Doppler frequency $\omega_{d2}$ is obtained by adding it to the differential Doppler frequency $\Delta\omega_1$. That is, $$\omega_{d2} = \Delta\omega_1 + \omega_{d1}.$$

Thus, it is possible to obtain successively Doppler frequencies $\omega_{di}$ by repeating the similar processing. That is, the Doppler frequency $\omega_{d,i+1}$ corresponding to the (i+1)-th repetition pulse can be obtained by using the Doppler frequency $\omega_{di}$ corresponding to the i-th repetition pulse and the differential Doppler frequency $\Delta\omega_i$, as indicated by the following equation:

$$\omega_{d,i+1} = \Delta\omega_i + \omega_{di} \qquad (14)$$

In the case where it is desired to obtain the speed, since the speed is in proportional relationship to the Doppler frequency, it can be obtained at the output E of the converter 19 by giving the frequency/speed converter 19 the output of the terminal C.

The above-mentioned embodiment of this invention will be explained in more detail, referring to FIGS. 6A 6B, 7A, 7B, 7C and 7D. B and C in FIGS. 7A and 7C correspond to the Doppler frequency obtained by the prior art technique and to that obtained by the method according to this invention at the terminals B and C in FIG. 5, respectively.

Figure 6A:
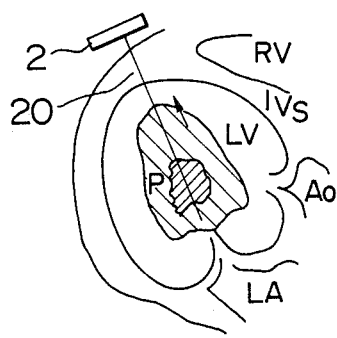
FIGS. 6A, 6B, 7A, 7B, 7C, 7D, 8A, 8B and 8C are diagrams useful for explaining this invention.
Figure 7A:
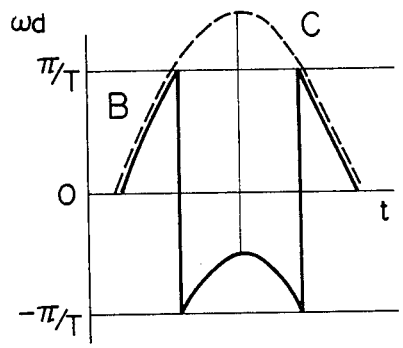

FIG. 6A is a diagram illustrating a measurement of the speed of the blood flow, in which 2 is a ultrasonic probe; 20 indicates the direction of the beam; P is a measurement point in question; LA is the left atrium; RV is the right ventricle, $A_0$ is an artery; IVS is the interventricular septum; and the arrow shows the direction of the blood flow. FIG. 7A shows variations in the speed with respect to time at the point P and B indicated by a solid line (i.e. $\omega_d$ measured by the prior art method) shows that the Doppler frequency $\omega_d$ exceeds $\pi/T$ and aliasing is produced, because the speed of the blood flow is high.

Figure 7C:
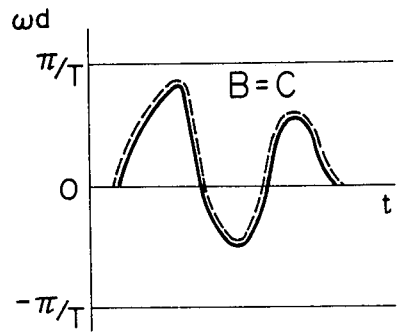
Figure 7B:
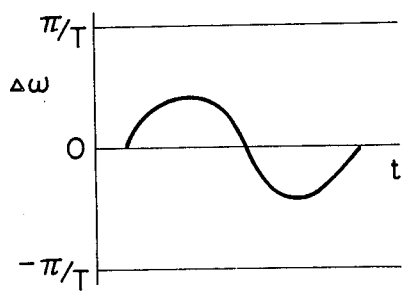

FIG. 7B shows variations in the differential Doppler frequency at the point P with respect to time, where no aliasing is produced. The Doppler frequency C obtained from the differential Doppler frequency by using the above-mentioned Eq. (4) is not subjected to aliasing, as indicated by the dotted line C in FIG. 7A.

Figure 6B:
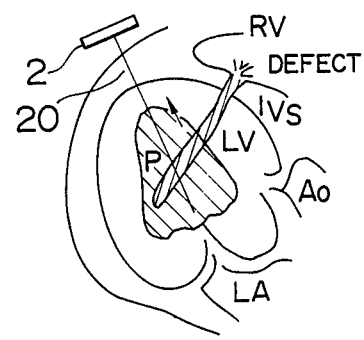
Figure 7D:
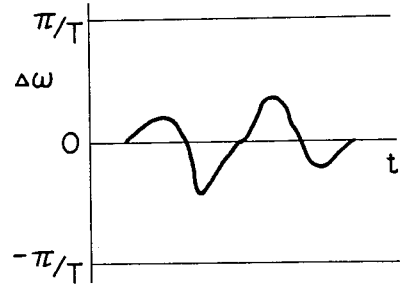

On the other hand, FIG. 6B shows the variations, in the case where no aliasing is produced and there exists an abnormal blood flow. This is a case where a reverse flow due to an interventricular septal defect is produced. FIGS. 7C and 7D show variations in the Doppler frequency and the differential Doppler frequency, respectively, with respect to time in this case. In this case the Doppler frequency B is not subjected to aliasing and the Doppler frequency C is obtained on the basis of the differential Doppler frequency.

In the speed measurement method according to this invention, the output $\omega_{do}$ obtained at the beginning of the speed measurement by the $\omega_{di}$ operator 18 is used as the initial value, on the basis of which following speed measurements are effected. Consequently, if no aliasing is produced for $\omega_{di}$ just at the beginning of the speed measurement, even if it is produced thereafter, it has no bad influences on the speed measurement.

In the measurement of the blood flow speed, since the blood flow pulsates, accurate measurement is possible if the measurement is started by giving the control signal to the control terminal D in FIG. 5 at a timing such that the speed is low and no aliasing is produced.

Although the Doppler frequency and the differential Doppler frequency are calculated by autocorrelation in the above explanation, they can be obtained by various operation methods. For example the method proposed in U.S. Ser. No. 101,444, filed Sept. 28, 1987 (corresponding to JP-A-63-84533 laid-open Apr. 15, 1988), in the name of the same assignee may be used therefor. That is, at first a phase angle operator is disposed at the output of the MTI filter 12 and the phase angles $\theta_i$ of the received signals $V_i$ are successively calculated. At the same time the phase differences $\Delta\theta_i$ $(=\theta_{i+1}-\theta_i)$ are decomposed into two-axial components on orthogonal coordinates, i.e. X-axis components ($\cos \Delta\theta_i$) and Y-axis components ($\sin \Delta\theta_i$). Then the mean value of the X-axis components $\overline{X}=(\Sigma\cos \Delta\theta_i)/n$ and of the Y-axis components $\overline{Y}=(\Sigma\sin \Delta\theta_i)/n$ (n denotes a predetermined number of ultrasonic wave pulses) are obtained, from which the mean phase difference $\overline{\Delta\theta_i}=\tan^{-1}(\overline{Y}/\overline{X})$ is calculated. An operator corresponding to the $\omega_{di}$ operator 18 calculates $\overline{\Delta\theta}/T$ therefrom and obtains the initial value $\theta_{d0}$ of the Doppler frequency. Further, $\overline{\Delta\Delta\theta_i}$ are successively calculated by a similar method from $\overline{\Delta\theta_i}$ obtained as described above and $\Delta\omega_{di}$ are obtained successively by effecting operations $\overline{\Delta\Delta\theta_i}/T$ therefrom. On the basis of $\omega_{d0}$ and $\Delta\omega_{di}$ thus obtained the accumulation ($\omega_{di}=\Delta\omega_{di}+\omega_{d0}$) is effected according to this invention indicated in FIG. 4 and the Doppler frequencies at various points of times are calculated one after another.

Further, although explanation has been made on the case where the differential Doppler frequency is used as the acceleration, it is possible also to obtain the acceleration from the gradient of a Doppler frequency curve (linear line) obtained by interpolating the Doppler frequency by the linear approximation using a plurality of Doppler frequencies.

Figure 9:
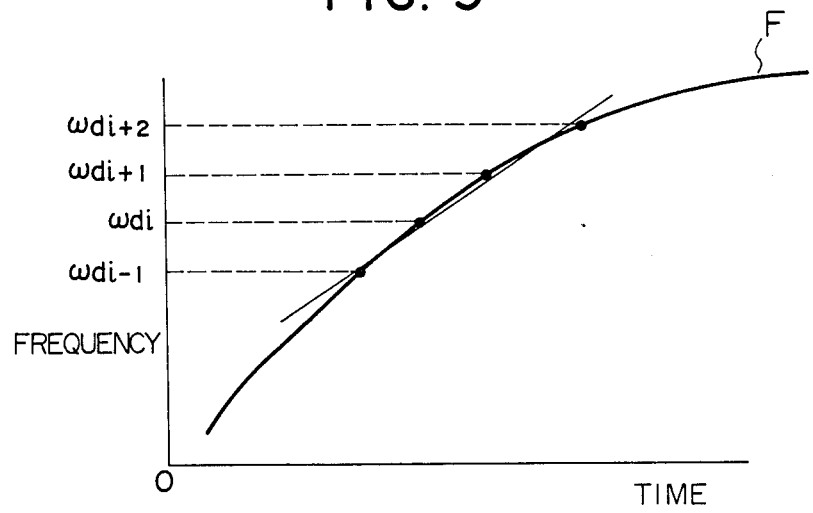
FIG. 9 is a diagram useful for explaining an alternative example of a part of the Doppler meter, which is an embodiment of this invention.

FIG. 9 is a scheme for explaining the method described above. In the figure differential Doppler frequencies $\Delta\omega_{di}$ $(=\omega_{d,i+1}-\omega_{di})$ are approximated by the gradient of a straight line F fitting 4 points in total of $\omega_{d,i+1}$, $\omega_{di}$, and $\omega_{d,i+2}$ and $\omega_{d,i-1}$ plotted before and after these two points, respectively.

In the above explanation the whole construction of the ultrasonic diagnosis apparatus, e.g. the transmission/reception deflecting circuit of the sector scanner, the display device, etc. are omitted.

This invention is useful for the Doppler flow speed measurement by a flat plane type probe and a mechanical scanner using it, a sector and a linear electron scanning type device, etc.

Further, although the above explanation has been made utilizing ultrasonic waves, this invention is valid for general waves such as light, electromagnetic waves, laser, etc.

As explained above, according to this invention, it is possible to measure accurately a high blood flow speed exceeding the limit determined by the interval of transmitted pulses and therefore diagnostic merit thereof is great.

Further, as another effect, the difference between phase differences obtained according to this invention corresponds to the acceleration of the blood flow and therefore it is useful for evaluation of the function of the heart such as the left ventricular systole.

We claim:

1. An ultrasonic Doppler apparatus comprising:
   transmitting/receiving means for transmitting ultrasonic bursts at constant time intervals towards an object one after another, for receiving reflected waves from said object and for generating reception signals;
   means for obtaining a first phase difference vector representing a phase difference between the phase of a current reception signal and that of a preceding reception signal, and producing an output signal indicative of said first phase difference vector;
   means for obtaining a second phase difference vector representing a phase difference between a current first phase difference vector and a preceding first phase difference vector, and producing an output signal indicative of said second phase difference vector; and
   means for deriving the velocity of said object from said first phase difference vector and said second phase difference vector.

2. An ultrasonic Doppler apparatus according to claim 1, wherein said velocity deriving means includes:
   means for deriving a Doppler frequency from said first phase difference vector and producing and output signal indicative thereof;
   means for deriving a differential Doppler frequency from said second phase difference vector and producing an output signal indicative thereof;
   accumulating means for adding a current output signal of said differential Doppler frequency deriving means to a preceding output signal of said Doppler frequency deriving means to obtain a current Doppler frequency; and
   converting means for converting said current Doppler frequency into the velocity of said object.

3. An ultrasonic Doppler apparatus according to claim 2, wherein said accumulating means comprises:
   means for adding a plurality of inputs, one of said plurality of inputs being said output signal indicative of said differential Doppler frequency, and producing an output signal indicative of the sum of said plurality of inputs;
   means for delaying the output of said adding means;
   means for switching another of said plurality of inputs of said adding means between said output of said Doppler frequency deriving means and said delayed output of said adding means; and
wherein said switching means supplies said adding means with an initial output of said Doppler frequency deriving means at a beginning of said velocity measurement and supplies said adding means with said delayed output of said adding means thereafter.

* * * * *